(12) United States Patent
Wohlfarth

(10) Patent No.: US 8,641,493 B2
(45) Date of Patent: Feb. 4, 2014

(54) COOLING DEVICE FOR THE AIR CONDITIONING OF AN EXAMINATION AREA OF A MEDICAL EXAMINATION APPARATUS AND MEDICAL EXAMINATION APPARATUS COMPRISING A COOLING DEVICE

(75) Inventor: Katrin Wohlfarth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1382 days.

(21) Appl. No.: 12/380,153

(22) Filed: Feb. 24, 2009

(65) Prior Publication Data
US 2009/0215384 A1  Aug. 27, 2009

(30) Foreign Application Priority Data
Feb. 25, 2008  (DE) .................. 10 2008 010 937

(51) Int. Cl.
*F24F 13/06*  (2006.01)

(52) U.S. Cl.
USPC ........................................ 454/254; 454/258

(58) Field of Classification Search
USPC .............. 454/187–189, 256, 258, 284
See application file for complete search history.

(56) References Cited

U.S. PATENT DOCUMENTS

| | | | | |
|---|---|---|---|---|
| 5,004,149 A * | 4/1991 | Narikiyo et al. | .............. | 236/49.3 |
| 6,516,282 B2 * | 2/2003 | Hedlund et al. | .............. | 702/132 |
| 6,550,686 B2 * | 4/2003 | Kawai et al. | .............. | 236/49.3 |
| 7,495,442 B2 * | 2/2009 | Heid | .............. | 324/318 |
| 7,498,807 B2 * | 3/2009 | Tigwell | .............. | 324/307 |
| 7,764,180 B2 * | 7/2010 | Huang | .............. | 340/573.1 |
| 8,035,385 B2 * | 10/2011 | Tomiha et al. | .............. | 324/318 |
| 2005/0030028 A1 | 2/2005 | Clarke et al. | | |
| 2007/0114292 A1 * | 5/2007 | Breed et al. | .............. | 236/49.3 |
| 2008/0006709 A1 * | 1/2008 | Ashworth et al. | .............. | 236/1 C |
| 2008/0314566 A1 * | 12/2008 | Chen et al. | .............. | 165/104.33 |
| 2009/0134874 A1 * | 5/2009 | Katsunuma et al. | .............. | 324/318 |

FOREIGN PATENT DOCUMENTS

| | | | | |
|---|---|---|---|---|
| DE | 102004038237 A1 | 3/2005 | | |
| JP | 01303131 A | * 12/1989 | .............. | A61B 6/03 |
| JP | 01303131 A1 | 12/1989 | | |
| WO | PCT/EP2000/008971 | * 2/2000 | .............. | G01R 33/28 |
| WO | PCT/EP2000/008971 | * 9/2000 | .............. | G01R 33/28 |
| WO | 0164468 A1 | 9/2001 | | |

* cited by examiner

*Primary Examiner* — Steven B McAllister
*Assistant Examiner* — Ko-Wei Lin

(57) ABSTRACT

An inventive cooling device for the air conditioning of an examination area of a medical examination device includes a temperature detection device for detecting a temperature in the examination area, an air conditioning device for producing air-conditioned air, an air discharge device arranged within the examination area, an opening directed toward the examination area to let out air-conditioned air and an air duct to transport air-conditioned air to the opening in the air discharge device and a control unit connected to the temperature detection device and the air-conditioning device to control the air-conditioning device based on data detected by the temperature detection device. The cooling device automatically determines and regulates a temperature in the examination area with fresh, air-conditioned air which has a positive influence on the well-being of the patient in the examination area.

11 Claims, 1 Drawing Sheet

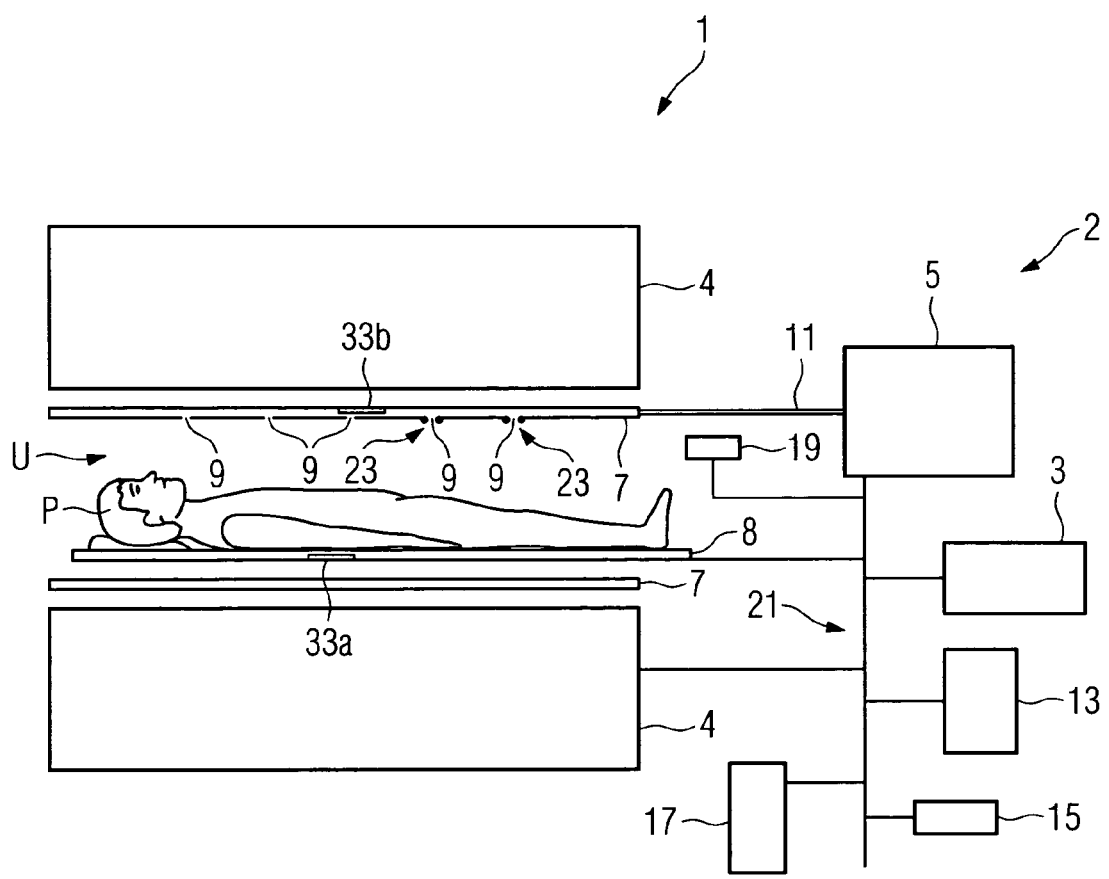

COOLING DEVICE FOR THE AIR CONDITIONING OF AN EXAMINATION AREA OF A MEDICAL EXAMINATION APPARATUS AND MEDICAL EXAMINATION APPARATUS COMPRISING A COOLING DEVICE

CROSS REFERENCE TO RELATED APPLICATIONS

This application claims priority of German application No. 10 2008 010 937.1 filed Feb. 25, 2008, which is incorporated by reference herein in its entirety.

FIELD OF THE INVENTION

The invention relates to a cooling device for the air conditioning of an examination area of a medical examination apparatus and a medical examination apparatus comprising such a cooling device.

BACKGROUND OF THE INVENTION

During an examination with a medical examination apparatus such as a computed tomography device (CT device), a radiation therapy device or a magnetic resonance device, the patient to be examined is situated in an examination area inside the medical examination apparatus. As a rule patients already find being examined a stressful experience. In addition, during the examination the temperature prevailing in the examination area often increases as a result of the examination and the patient's body heat. The patient generally finds this unpleasant and this increases the stress and unease that the patient experiences. Furthermore, the air in the examination area is normally still and therefore easily starts to feel oppressive and, the fact that the examination area frequently seems cramped contributes to this. This often leads to a patient becoming increasingly agitated.

Magnetic resonance technology (hereinafter the abbreviation MR is used to stand for magnetic resonance) is a known technique, by means of which images from inside an examination object can be produced. Simply expressed, the examination object is positioned in an MR unit in a comparatively strong, static, homogenous main magnetic field (field strengths from 0.2 Tesla to 7 Tesla and more) so that its nuclear spins are oriented along the main magnetic field. To trigger nuclear spin resonances, high frequency excitation pulses are radiated onto the object to be examined, the triggered nuclear spin resonances are measured and based on this, image and/or spectroscopy data of the examined object, for example, are reconstructed. For position coding of the measurement data rapidly switched magnetic gradient fields are quickly superimposed on the main magnetic field.

During an examination with a magnetic resonance device (MR examination), the temperature in the magnetic resonance device can increase in particular due to the high frequency alternating fields that have to be applied. Various factors have an influence on the temperature in an examination area, in particular in a magnetic tube, of the magnetic resonance device. Some of these factors are, for example, the main magnetic field strengths, the duration of the respective examination and the duration of an individual measurement, the examination sequence used, the room temperature surrounding the magnetic resonance device and also, of course, the patient himself/herself.

In order to prevent the patient from becoming too warm during an MR examination, generally an air flow is produced which is designed to cool the patient generally with the aid of a ventilator arranged at the entry or exit of the magnetic tube of a cylindrical magnetic resonance device or adjacent to an open magnetic resonance device. In such cases only the strength of the air flow produced by the ventilator can be varied and the ventilator may be switched off if required, so as to adapt to the patient's wishes and requirements.

This method is, however, often insufficient, for example, in preventing the patient from sweating which is unpleasant. In addition, the air flow cannot be optimally controlled which means that this often cannot reach as far as the examination center of the examination area of a medical examination apparatus. It is precisely there where the temperature increases the most during an examination. Therefore pauses during the examination may be necessary in which the patient is moved out of the medical examination apparatus until the temperature in the examination area has dropped again.

SUMMARY OF THE INVENTION

The object of the present invention is therefore to specify a cooling device for the air conditioning of an examination area of a medical examination apparatus, which can ensure that the patient is comfortable during an examination and at the same time makes the examination very efficient.

The object is achieved by a cooling device for the air conditioning of an examination area of a medical examination apparatus as well as by a medical examination apparatus as claimed in the claims.

The inventive cooling device for the air conditioning of an examination area of a medical examination apparatus comprises a temperature detection device for detecting a temperature prevailing in the examination area, an air conditioning device for producing air conditioned air, an air discharge device arranged inside the examination area, which comprises at least one opening directed toward the examination area to let out the air produced by the air conditioning device, and at least one air duct for transporting air-conditioned air from the air conditioning device to the openings in the air discharge device and a control unit connected to the temperature detection device and the air conditioning device for controlling the air conditioning device on the basis of data detected by the temperature detection device.

One such cooling device enables automatic determination and regulation of a temperature prevailing in the examination area. At the same time, the examination area is provided with fresh, air-conditioned air. Both effects have a positive influence on the well-being of the patient in the examination area. If the patient to be examined with the medical examination apparatus is more comfortable, this also has a positive effect on the quality of the examination results. For example, a patient who is feeling comfortable does not move as much during an examination as a restless patient who feels ill at ease. This increases, for example, the quality of image recordings in the context of an examination by means of an imaging medical examination apparatus, since movement artifacts in the recordings can be avoided from the outset.

Furthermore, through constant regulation of the temperature in the examination area during an examination, the time required for the examination can be shortened. This is because there is no longer a need for examination pauses between individual measurements to allow the patient and also the examination area and/or the medical examination apparatus to cool down. In particular in magnetic resonance devices with basic magnetic fields of, nowadays, 3 to 7 Tesla, such examination pauses have until now been customary.

Further advantages of the inventive cooling device arise for assessing the Specific Absorption Rate (SAR) which is a measure of the absorption of electromagnetic fields in biological tissue. In known SAR assessment procedures the temperature of the examination area of a medical examination apparatus also has an influence. By means of the inventive cooling device, current prevailing temperature data are always available and the assessment can be carried out very accurately. In this way, the assessment can be less restrictive since the estimated value has minor errors and can therefore approach a valid maximum value, without the risk of said maximum value actually being exceeded.

In addition a lower temperature in the examination area causes a reduction in the prevailing absorption rate. Again, this can reduce the number of pauses during the examination and in particular in magnetic resonance devices can enable examination sequences with strong electromagnetic alternating fields.

Advantageously, the control unit of the cooling device is connected to an input unit. Thus, for example, target values and/or tolerances for the temperature prevailing in the examination area can be adapted to the individual wishes of a patient or particular examination sequences. In particular during an examination, this can either be carried out by staff overseeing the examination or directly by the patient himself/herself. Appropriate input units are known.

In an advantageous embodiment openings in the air discharge device comprise air quantity regulation devices for regulating an air through-flow quantity. This can be done for example by the diameter of the openings being able to be regulated by the air quantity regulation devices and/or the pressure of the air-conditioned air being able to be varied by the cooling device at the openings. This means that an air draft caused by the flowing air-conditioned air and the volume of air-conditioned air flowing in a period of time can easily be regulated.

In a further advantageous embodiment, the cooling device comprises a position determination device connected to the control device for determining a position of a part of the body of a patient located in the examination area. On the basis of this position information, the control unit can control the cooling device easily in such a way that an air draft caused by inflowing air-conditioned air does not contact the part of the patient's body directly or only slightly, the position of said body part having been determined. This can be done for example by openings in the air discharge device which are directed toward the position of the part of the body being closed, made narrower or diverted. Possible position-determining devices are, for example, cameras, light-beam localizers or other known devices for position-determining in medical examination apparatus. Also, a so-called adjustment scan can frequently be used for this prior to examinations by means of imaging medical examination apparatus, such as magnetic resonance devices.

Patients often find it particularly unpleasant if a draft of air hits them directly in the face. It is therefore particularly advantageous to determine by means of the position determining device a position of the head or the face of a patient in the examination area and thus by means of the control unit to prevent "blasting" thereof.

In a further embodiment of the cooling device, the control unit is connected to a monitoring unit by means of a data link, which controls an examination to be carried out by the medical examination apparatus. In this way, the control unit can easily obtain information, even prior to the start of a next examination sequence, about the duration of the examination and/or the planned method of examination, in particular the MR sequences used. From this information, a temperature characteristic in the examination area can be calculated or estimated in advance without temperature regulation and corresponding, counter-controlling measures, e.g. in the form of rule commands can be initiated at the air conditioning device. In this way, the temperature constantly remains at a desired value. The cooling device no longer reacts just to the temperature changes produced but can regulate the temperature in advance.

The advantages and embodiments described regarding the cooling device apply similarly to the medical examination apparatus.

BRIEF DESCRIPTION OF THE DRAWINGS

Further advantages and details of the present invention emerge from the exemplary embodiments described in the following and with reference to the drawings. The examples given do not limit the invention in any way.

FIGURE shows schematically a medical examination apparatus according to the invention with an inventive cooling device of a magnetic resonance device in the example.

DETAILED DESCRIPTION OF THE INVENTION

The FIGURE shows in a schematic representation an inventive medical examination apparatus of a magnetic resonance device 1 in the example comprising an inventive cooling device 2.

The magnetic resonance device 1 comprises a magnetic unit 4, which again comprises in a known manner at least one main magnet and gradient coils to excite magnetic resonance signals in an examination object, as well as a monitoring unit 17 to control the magnetic resonance device 1 and a bed 8 for supporting an object to be examined, such as a patient P. Furthermore the magnetic resonance device 1 comprises an examination area U for recording an examination object, which is surrounded by the magnetic unit 4 and in which fields required for an examination can be produced. Additional parts of the magnetic resonance device 1 such as high frequency and local coils are known and are not shown for the sake of clarity.

The cooling device 2 comprises a temperature detection device 3, an air conditioning device 5, an air discharge device 7, which is arranged in the examination area U and at least one opening 9 directed toward the examination area U, as well as at least one air duct from the air conditioning device 5 to the air discharge device 7, and furthermore a control device 13 connected for exchange of data, for example with all the parts listed but in particular with the temperature detection device 3. Expediently the cooling device 2 is further connected to an input unit 15, from which a target value and/or tolerances for the temperature in the examination area U can be given to the control unit 13, for example by the staff looking after the examination or directly by a patient being examined. Input units of this type are already known. Furthermore, they also enable, for example, an input related to a desired pressure value, with which air-conditioned air should leave the openings 9.

The temperature detection device 3 detects a temperature prevailing in the examination area U. For this purpose, the temperature detection device 3 for example comprises temperature sensors 33a, 33b which are arranged inside the examination area U and are connected to the temperature detection device 3 via data links 21. Possible temperature sensors comprise, for example, optical sensors, pyrometers or other known temperature measuring sensors. Attention may need to be paid to compatibility with the medical examination apparatus. The temperature sensors 33a, 33b can be arranged particularly simply on the bed 8 of the medical examination apparatus 1 or on the air discharge device 7 or on the cladding of the medical examination apparatus directed toward the examination area.

In another exemplary embodiment, the temperature detection device 3 comprises the magnetic resonance device 1 which has temperature-sensitive measuring sequences. The temperature detection device 3 receives detected temperature data for further utilization via a data link 21 to the magnetic resonance device 1 and/or the monitoring unit 17 in each case by means of the magnetic resonance device 1.

The air conditioning device 5 is for example at least a part of an air conditioning system already present for the whole examination area or for the overall medical device, in which the medical examination apparatus 1 is located. Alternatively the air conditioning device 5 can also represent an independent system for the production and/or maintenance of a temperature, air humidity and/or air quality that can be set. Such systems are known from air conditioning system technology. Advantageously at least one temperature of the air-conditioned air produced can be influenced by the air conditioning device 5. In a simple case, the air conditioning device can also simply transport fresh air, e.g. from outside the building in which the medical examination apparatus is situated or from the area surrounding the medical examination apparatus, via air ducts 11 to the air discharge device 7 as air conditioned air.

The control unit 13 controls the air conditioning device 5 on the basis of data detected by the temperature detection device 3 relating to the temperature in the examination area U in such a way, that a preset value, e.g. through input by means of the input device 15, can be achieved or maintained for the temperature in the examination area. In particular if the detected temperature value exceeds the desired value in the examination area U during the examination, the control unit 13 triggers the air conditioning device 5 to feed colder air via the air discharge device 7 into the examination area U, in order to reduce the temperature there to the desired value.

The air discharge device 7 comprises at least one opening 9 directed toward the examination area U, through which the air-conditioned air produced by the air conditioning device 5 can enter the examination area U. The more openings 9 the air discharge device 7 comprises, the more evenly and/or accurately the air-conditioned air can be distributed in the examination area U. Correspondingly the number and distribution of openings 9 around the examination area U can be selected according to the particular requirements. In this case at least one opening 9 is expediently arranged close to the center of the examination area U, since it is there in particular where the largest increase in heat takes place during an examination.

In a simple exemplary embodiment, the air discharge device 7 is implemented by a cladding of the examination device directed toward the examination area U, which is at least partially embodied as hollow, so that the air-conditioned air can travel through the hollow passages thus formed to the openings 9 and enter the examination area U. Alternatively, the air discharge device 7 can for example be embodied by a tube system arranged in the examination area U or by another air ducting system.

In a further exemplary embodiment the openings 9 of the air discharge device 7 have air quantity regulation devices 23 to regulate an air through-flow quantity through the openings 9. Such air quantity regulation devices 23 can for example be embodied in the form of jets with variable diameter and/or angles of inclination which allow regulation of the air through-flow quantity. However, a simple opening and closing mechanism at least of individual openings 9 is conceivable which allows regulation of an air draft caused by incoming air-conditioned air as well as an inflow volume of air-conditioned air in terms of time.

The air quantity regulation devices 23 are for example connected to the control unit 13 by means of data links 21 which can control the air through-flow quantity of the individual openings by means of the air regulation devices 23. This control takes place for example on the basis of data which the control unit 13 receives from a monitoring unit 17 to control the medical examination apparatus 1. For this purpose, the control unit 13 is connected to a monitoring unit 17 via a data exchange link 21 and receives for example data about an examination to be carried out. In this way, the control unit 13 can in particular receive data about expected positions of the patient P in the examination area U at different times of the examination and control the air quantity regulation devices 23 in such a way that in each case only a particular part of the patient P is blasted with air-conditioned air.

Further data which the control unit 13 can obtain from the monitoring unit 17 to control the air conditioning device 5 are the planned duration of the medical examination, the type of examination and/or in the case of a magnetic resonance device as an examination device, the examination sequence. On the basis of this data, the control unit 13 can assess in advance the temperature changes to be expected in the examination area U and arrange for the air conditioning device 5 to take countermeasures.

In a further embodiment, the control unit 13 is further connected to a position determining device 19 in order to obtain the most precise data possible about the positions of the patient P or of the parts of the body of the patient P in the examination area U during the examination. As already described, this data can be used by the control unit 13 to control the air conditioning device 5 and/or the air quantity regulation devices 23.

A determination of the position of the face of a patient during the examination and a corresponding control of the air conditioning device 5 or air quantity regulation devices 23 in particular such that the face is not blasted with cold air through the air discharge device 7 in an unpleasant manner, considerably increase the comfort for the patient P.

Position determining devices 19 include for example cameras or, in medical examination apparatus, usual light-beam localizers which have been used conventionally to determine the position of the patient P. A further possibility for obtaining position data for the patient is to carry out a so-called adjustment scan as is usual in imaging medical examination devices. To transmit this data, the position determining device 19 is connected to the control unit 13 via data links 21.

Data links 21 as quoted in the example can be wired or BUS links as well as wireless links such as radio, bluetooth or infrared connections. The data links 21 are shielded if necessary or otherwise adapted to use in connection with the medical examination apparatus 1.

A further positive effect of the invention is that at the same time as the examination area U is cooled, so is the environment of the examination area U which can have a positive influence on the effectiveness of the medical examination apparatus 1. In a magnetic resonance device 1, for example, this can also affect gradient and high frequency coils in particular which can operate more effectively through cooling.

The invention claimed is:
1. A cooling device for conditioning air of an examination area of a medical examination apparatus, comprising:
 a temperature detection device that detects a temperature in the examination area;

an air conditioning device that produces air-conditioned air;

an air discharge device arranged within the examination area comprising an opening directed toward the examination area that discharges the air-conditioned air into the examination area surrounded by a magnetic unit of the medical examination apparatus;

an air duct that transports the air-conditioned air from the air conditioning device to the opening in the air discharge device; and a control unit connected to the temperature detection device and the air conditioning device that controls the air conditioning device based on data detected by the temperature detection device, wherein the air discharge device is integrated in a cladding of the medical examination apparatus directed toward the examination area; a position determining device connected to the control unit that determines a position of a body part of a patient in the examination area; and wherein the air conditioning device is controlled by the control unit based on the determined position.

2. The cooling device as claimed in claim 1, wherein the control unit is connected to an input unit that inputs an individual target value of the temperature in the examination area or a tolerance of the temperature in the examination area.

3. The cooling device as claimed in claim 1, wherein the temperature detection device comprises a temperature sensor arranged on a patient bed of the medical examination apparatus or on the air discharge device or on the cladding of the medical examination apparatus inside the examination area.

4. The cooling device as claimed in claim 1, wherein the opening of the air discharge device comprises an air quantity regulation device that regulates an air through-flow quantity.

5. The cooling device as claimed in claim 4, wherein the control unit is connected to the air quantity regulation device.

6. The cooling device as claimed in claim 1, wherein the position determining device determines a position of a face of the patient.

7. The cooling device as claimed in claim 1, wherein the position determining device comprises a camera.

8. The cooling device as claimed in claim 1, wherein the control unit is connected to a monitoring unit that monitors the examination.

9. The cooling device as claimed in claim 8, wherein the air conditioning device is controlled based on data monitored by the monitoring unit.

10. The cooling device as claimed in claim 1, wherein the medical examination apparatus comprises a magnetic resonance device.

11. A medical examination apparatus, comprising:

an examination area in which a patient to be examined is occupied;

a temperature detection device that detects a temperature in the examination area;

an air conditioning device that produces air-conditioned air;

an air discharge device arranged within the examination area comprising an opening directed toward the examination area that discharges the air-conditioned air into the examination area surrounded by a magnetic unit of the medical examination apparatus;

an air duct that transports the air-conditioned air from the air conditioning device to the opening in the air discharge device; and a control unit connected to the temperature detection device and the air conditioning device that controls the air conditioning device based on data detected by the temperature detection device, wherein the air discharge device is integrated in a cladding of the medical examination apparatus directed toward the examination area; a position determining device connected to the control unit that determines a position of a body part of a patient in the examination area; and wherein the air conditioning device is controlled by the control unit based on the determined position.

* * * * *